(12) United States Patent
Bullister et al.

(10) Patent No.: US 6,367,333 B1
(45) Date of Patent: Apr. 9, 2002

(54) NOTCH DIAPHRAGM PRESSURE SENSOR

(75) Inventors: Edward Theodore Bullister, Weston; Peter Richard d'Entremont, Walpole, both of MA (US); Sanford Reich, Providence, RI (US); Neil Silverman, Framingham, MA (US)

(73) Assignee: APEX Medical, Inc., East Walpole, MA (US)

( * ) Notice: Subject to any disclaimer, the term of this patent is extended or adjusted under 35 U.S.C. 154(b) by 0 days.

(21) Appl. No.: 09/726,865

(22) Filed: Nov. 30, 2000

Related U.S. Application Data

(63) Continuation-in-part of application No. 09/304,871, filed on May 4, 1999, now Pat. No. 6,171,253.

(51) Int. Cl.[7] ............................................. G01L 7/08
(52) U.S. Cl. ...................................................... 73/715
(58) Field of Search .......................... 73/706, 715–727, 73/730, 756; 600/486, 488, 561, 300; 128/897, 898, 899; 137/487.5, 557

(56) References Cited

U.S. PATENT DOCUMENTS

| | | |
|---|---|---|
| 2,420,148 A | 5/1947 | Ostergren |
| 4,218,926 A | 8/1980 | Devisser |
| 4,398,542 A | 8/1983 | Cunningham et al. |
| 4,483,196 A | 11/1984 | Kurtz |
| 4,825,876 A | 5/1989 | Beard |
| 4,840,068 A | 6/1989 | Mayhew, Jr. |
| 5,000,049 A | 3/1991 | Cooper et al. |
| 5,410,916 A | 5/1995 | Cook |
| 5,505,092 A | 4/1996 | Kowalski |
| 5,564,434 A | 10/1996 | Halperin et al. |
| 5,602,339 A | 2/1997 | Wareham |
| 5,708,210 A | 1/1998 | Gardellin |
| 5,756,900 A | 5/1998 | Arie et al. |
| 6,024,704 A | 2/2000 | Meador et al. |
| 6,077,227 A * | 6/2000 | Miesel et al. ................ 600/486 |
| 6,116,269 A * | 9/2000 | Maxson .................... 137/487.5 |
| 6,171,235 B1 * | 1/2001 | Bullister et al. ............... 73/730 |

OTHER PUBLICATIONS

Iijima et al, "Control of Centrifugal Blood Pump Based on the Motor Current," Artificial Organs, vol. 21, No. 7, 11/97, pp: 655–660.
Freidrich et al, "Occlusive Thrombus Formation on Indwelling Cathers: In Vitro Investigation and Computational Analysis," Thrombosis and Haemostasis, vol. 73, No. 1, 1995, pp: 66–72 (no mo.).
Weltens et al, "Optimization of Catalytic Converter Gas Flow Distribution by CFD Prediction," SAE Paper 930780, Mar. 1–5, 1993, pp: 131–151.
"Proceedings Sensors Expo." May 19–21, 1998, p. 498.

* cited by examiner

*Primary Examiner*—William Oen
(74) *Attorney, Agent, or Firm*—Francis L. Conte

(57) ABSTRACT

A pressure sensor includes a tube for channeling a fluid therethrough. A notched seat is disposed in an outer surface of the tube and is open at circumferentially opposite ends, with a flexible diaphragm at the bottom thereof. The diaphragm is planar, and blends at its perimeter coextensively with an arcuate inner surface of the tube. A gauge is mounted in the seat above the diaphragm for measuring flexure thereof under pressure of the fluid inside the tube.

13 Claims, 7 Drawing Sheets

NOTCH DIAPHRAGM PRESSURE SENSOR

This application is a continuation-in-part of U.S. patent application Ser. No. 09/304,871 filed May 4, 1999, now U.S. Pat. No. 6,171,253.

This invention was made under United States Government support under Cooperative Agreement No. 70NANB7H3059 awarded by NIST. The United States Government has certain rights in the invention.

BACKGROUND OF THE INVENTION

The present invention relates generally to pressure sensors, and, more specifically, to through-flow pressure sensors.

Many types of pressure sensors are available for measuring pressure of a fluid flowing through a conduit. These sensors vary in complexity and operation and their affect on the fluid flow therethrough. The fluid may be compressible gas or incompressible liquid which may flow under laminar or turbulent flow conditions.

In the medical field pertaining to living patients, pressure sensing of bodily fluids introduces the additional requirement of patient safety. For example, the measurement of blood pressure must not damage the blood itself or form clots therein which are detrimental to patient health.

Artificial heart pumps are being developed in the exemplary form of a Left Ventricular Assist Device (LVAD) which assists damaged hearts. Typical artificial heart pumps are configured for varying blood flowrate, frequency, and pressure as required to meet the typical demands placed on the heart which change in response to work efforts. It is therefore desirable to control the heart pump by sensing blood pressure in the body. However, blood pressure must be measured without adversely affecting blood flow or causing damage or clotting thereof.

Furthermore, the sensing of blood pressure, in particular, requires high accuracy or resolution to precisely control the artificial heart pump. Blood pressure is typically measured in millimeters of mercury (Hg), with a blood pressure sensitivity of 1 mm Hg (0.02 psi) being desirable.

Accordingly, it is desired to provide an improved through-flow pressure sensor for use in precisely measuring pressure of a fluid, such as blood, without adversely affecting the flow thereof.

BRIEF SUMMARY OF THE INVENTION

A pressure sensor includes a tube for channeling a fluid therethrough. A seat is disposed in an outer surface of the tube, with a diaphragm at the bottom thereof. The diaphragm is planar, and blends at its perimeter coextensively with an arcuate inner surface of the tube. A gauge is mounted in the seat above the diaphragm for measuring flexure thereof under pressure of the fluid inside the tube.

BRIEF DESCRIPTION OF THE DRAWINGS

The invention, in accordance with preferred and exemplary embodiments, together with further objects and advantages thereof, is more particularly described in the following detailed description taken in conjunction with the accompanying drawings in which.

DETAILED DESCRIPTION OF THE INVENTION

Figure 1:
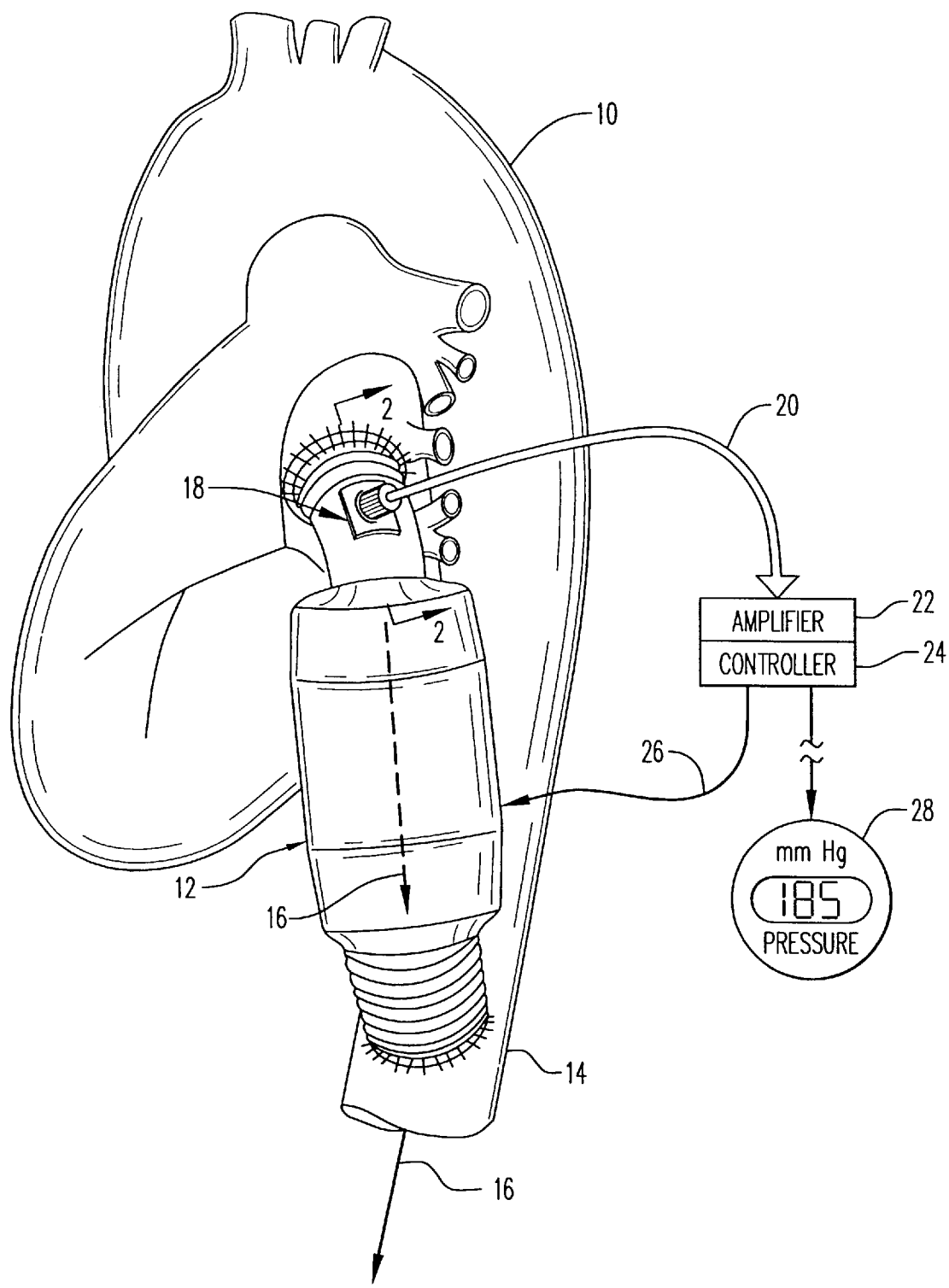
FIG. 1 is a schematic representation of a human heart including a heart assist pump joined thereto by an in vivo pressure sensor in the form of a cannula tube through which blood flows under pressure.

Illustrated schematically in FIG. 1 is a human heart 10 inside a living patient to which a Left Ventricular Assist Device (LVAD) or heart pump 12 is joined. The heart pump 1 2 may take any conventional form and is sutured in the patient, in this case between the left ventricle of the heart and the main artery or aorta 14 for assisting in pumping fluid or blood 16.

In accordance with the present invention, a tubular pressure sensor 18 joins the heart pump 12 in flow communication with the left ventricle for carrying blood through the pump while simultaneously measuring pressure thereof. The pressure sensor is operatively joined by an electrical cable 20 to a conventional amplifier 22 which in turn is operatively joined to an electrical controller 24 which controls operation of the heart pump 12 including its flowrate, frequency, and pumping pressure.

The controller 24 may take any conventional form and is operatively joined also to the heart pump 12 by another electrical cable 26 for controlling pumping of the blood 16 through the pump in response to measured pressure in the pressure sensor 18. The controller 24 is suitably configured for controlling blood flow through the pump 12 into the aorta 14, and may optionally be joined to a suitable pressure indicator 28 for permitting visual observation of the measured blood pressure which may be expressed in any suitable unit such as millimeters of mercury (mm Hg).

Figure 2:
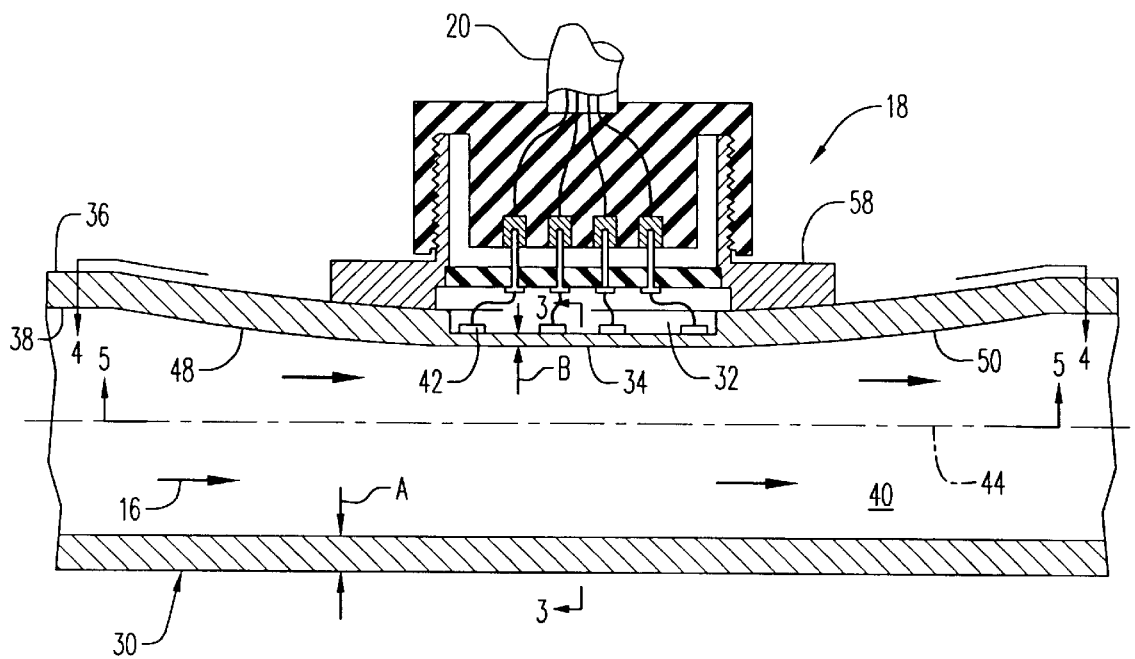
FIG. 2 is a longitudinal sectional view through the pressure sensor illustrated in FIG. 1 in accordance with an exemplary embodiment of the present invention, and taken along line 2—2.

The pressure sensor 18 is illustrated in longitudinal sectional view in FIG. 2 in accordance with an exemplary embodiment. The sensor includes a cannula tube 30 through which the blood fluid 16 is channeled. Since the fluid 16 in this exemplary embodiment is blood, the tube 30 is preferably formed of a hemo-compatible material such as titanium having proven benefits for carrying blood flow without incompatibility therewith. The tube is preferably smooth and seamless, with an annular thin wall having a nominal thickness A of about 39 mils (1.0 mm).

A recessed seat or pocket 32 is disposed in the wall of the tube, with a diaphragm 34 being disposed at the bottom of the seat. In accordance with the present invention, the diaphragm 34 is planar and flat, and is relatively thin and flexible having an exemplary thickness B of about 5 mils (0.1 3mm) which represents the difference between the nominal thickness of the tube wall and the depth of the seat 32 therein of about 34 mils (0.86 mm).

The tube has a radially outer surface 36 and an opposite, radially inner surface 38 which are arcuate, or circular for example. The inner surface defines the outer boundary of the bore or conduit 40 through which the fluid 16 flows.

Since the tube inner surface 38 is annular and the diaphragm 34 is flat, the tube is preferably configured for smoothly blending the diaphragm at or near its perimeter coextensively with the arcuate inner surface therearound. In this way, the inner surface of the tube remains smooth without discontinuity for promoting smooth flow of the fluid therealong without disruption.

Figure 3:
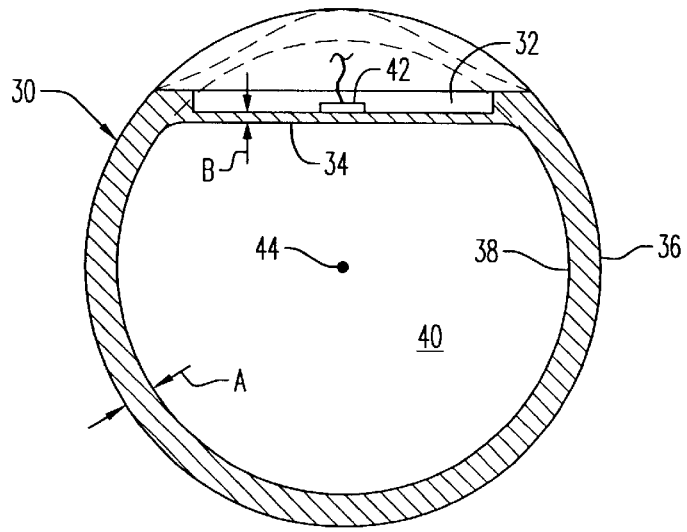
FIG. 3 is a radial sectional view through a diaphragm portion of the pressure sensor tube illustrated in FIG. 2 and taken along line 3—3.

As shown in FIGS. 2 and 3, means in the exemplary form of a gauge 42 are mounted in the seat above the diaphragm 34 for measuring flexure thereof under pressure inside the tube. In one embodiment, the flexure measuring gauge includes a plurality of strain gauges 42 mounted in the seat 32 atop the diaphragm 34 for measuring strain therein due to flexing of the diaphragm under pressure of the fluid 16 inside the tube. The strain gauges may take any conventional form and are typically adhesively bonded or joined by sputtering to the outer surface of the diaphragm in any suitable configuration, such as four in-line strain gauges.

The strain gauges are suitably electrically joined through the cable 20 to the amplifier 22 illustrated in FIG. 1 for producing an electrical voltage signal as the diaphragm is elastically deformed under pressure. The pressure of the fluid 16 inside the tube creates longitudinal and circumferential strain in the tube wall which is substantially greater in magnitude in the relatively thin diagram 34.

A diaphragm-based pressure sensor is conventionally known for a cylindrical pressure tube in which the diaphragm is arcuate. Since strain in the diaphragm is proportional to pressure acting thereon, internal pressure may be determined by measuring strain therein. For the conventional cylindrical tube with a complementary arcuate diaphragm, the measured pressure is directly proportional to the product of the modulus of elasticity of the tube material, the measured strain, and the thickness of the diaphragm, and inversely proportional to the radius of the tube.

However, by introducing the flat diaphragm 34 illustrated in FIGS. 2 and 3 in the otherwise cylindrical tube, a substantial increase in accuracy, sensitivity, and resolution of pressure measurement may be obtained. For a flat diaphragm supported around its perimeter, pressure on the diaphragm is similarly directly proportional to the modulus of elasticity and measured strain. However, the measured pressure is also directly proportional to the square of the thickness B of the diaphragm and a 4/3 product constant, and inversely proportional to the square of the distance of the strain gauges from the center of the flat diaphragm.

A simple comparison may be made between a cylindrical tube of radius 6.35 mm having an arcuate diaphragm of 0.076 mm thickness with a similar tube having a flat diaphragm of the same thickness with strain measured 3.2 mm from the center thereof. For the same material composition and minimum resolvable strain of 1.0 microstrain, the pressure resolution for the arcuate diaphragm is 10.3 mm Hg (0.2 psi), with the corresponding pressure resolution of the flat diaphragm being 0.67 mm Hg (0.013 psi). Accordingly, a similarly sized flat diaphragm affords a fifteen-fold improvement in pressure resolution or sensitivity as compared to the arcuate diaphragm.

In accordance with the invention, by the simple introduction of the flat diaphragm 34 extending both longitudinally and circumferentially in a portion of the tube, a substantially more precise pressure sensor may be obtained without adversely affecting or disrupting the fluid flow through the tube. However, a round tube is preferred for channeling blood to avoid any discontinuities or stagnation regions which could otherwise damage or lead to undesirable blood clotting. The flat diaphragm 34 must therefore be suitably blended into the otherwise round tube without introducing undesirable discontinuities therein.

More specifically, in the exemplary embodiment illustrated in FIGS. 2 and 3, the diaphragm 34 is integrally joined to the bottom of the seat 32 and is substantially flat around the perimeter of the seat. The seat itself may have any suitable configuration, with the circular seat being preferred for effecting a circular, flat diaphragm 34.

As shown in FIG. 3, the tube inner surface 38 is preferably arcuate or circular in section opposite to the flat diaphragm 34. And the diaphragm 34 forms a chord of the tube inner surface which blends smoothly therewith in a circumferential direction, with corresponding arcuate fillets formed between the circumferential edges of the diaphragm and the arcuate tube inner surface.

As shown in FIG. 2, the tube 30 has a longitudinal or axial centerline axis 44 and is round on opposite upstream, or forward, and downstream, or aft, longitudinal sides of the diaphragm 34. The tube inner surface 38 preferably smoothly blends longitudinally from round to flat on both longitudinal sides of the diaphragm for effecting a smooth transition without discontinuity.

Figure 4:
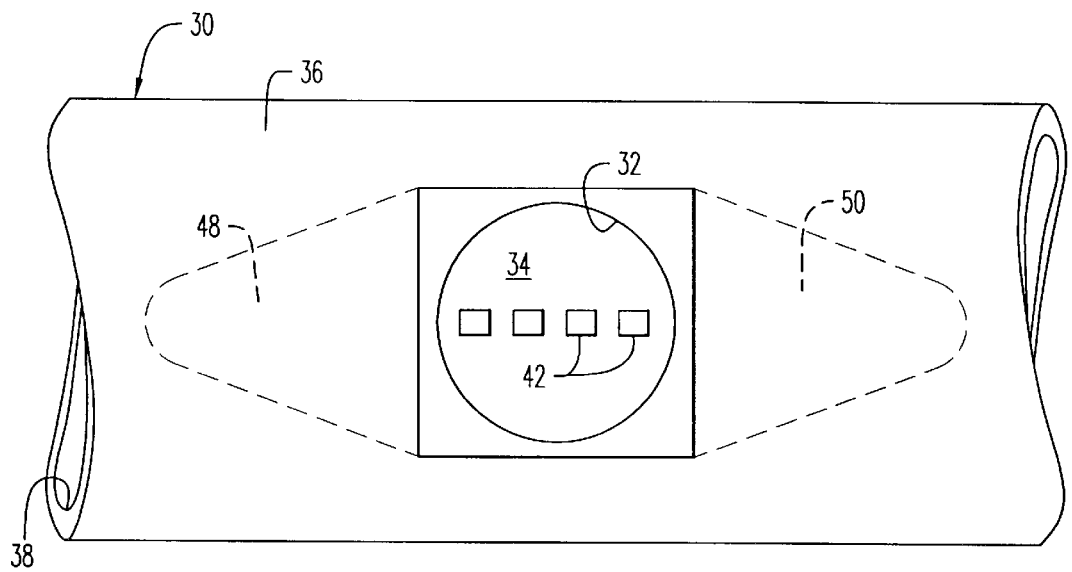
FIG. 4 is a top view of the tube and diaphragm illustrated in FIG. 2 and taken along line 4—4.
Figure 5:
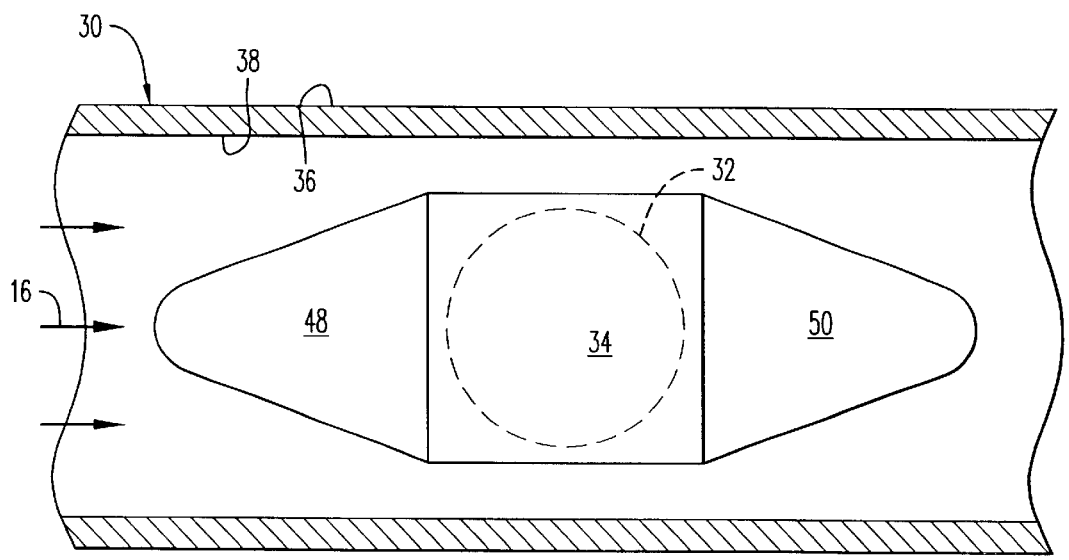
FIG. 5 is an outward facing view of the diaphragm and upper tube half illustrated in FIG. 2 and taken along line 5—5.

FIG. 2 illustrates a side sectional view through the tube 30 as the upper wall portion thereof transitions from round-to-flat-to-round along the downstream direction of fluid flow. FIG. 4 illustrates a top view of the circular seat 32 and the exemplary linear alignment of the four strain gauges 42 along the longitudinal axis of the tube which suitably transitions from round to flat to round along the upper wall. And, FIG. 5 is an inside view of the tube outer wall below the flat diaphragm 34 illustrating in more detail the round to flat to round transition along the tube inner surface 38.

Figure 6:
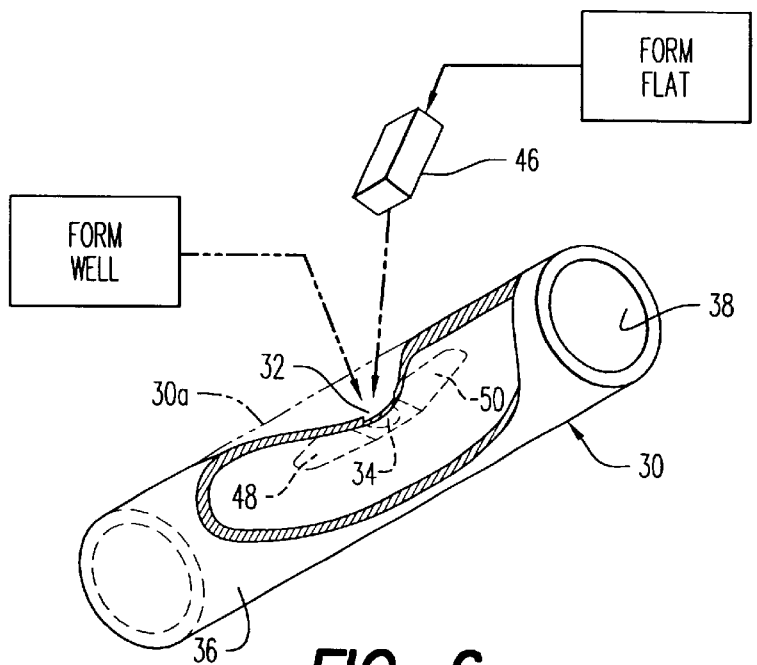
FIG. 6 is a schematic and flowchart representation of an exemplary method of forming the pressure sensor illustrated in FIGS. 1–5.

FIG. 6 illustrates schematically an exemplary method of forming the pressure sensor illustrated in FIGS. 1–5. An initially round or cylindrical tube, designated 30a, is plastically deformed at local portion thereof to form the flat diaphragm 34 along the chord of the circular cross section of the tube. This may be accomplished by using a square anvil 46 slightly larger in area than that of the intended circular seat 32. The anvil 46 is pressed against the outer surface of the tube for plastically deforming the tube radially inwardly and changing its contour locally from circular to flat immediately under the anvil 46.

Material may then be removed from the tube outer surface to form the corresponding seat 32 therein. This may be accomplished in any conventional manner such as milling or electrical discharge machining (EDM), in which the thin, flat diaphragm 34 remains as an integral portion of the tube itself. The seat may have any suitable form such as the cylindrical well illustrated, or a rectangular well. And, the seat may open at its circumferentially opposite sides to blend externally with the convex outer surface of the tube. The strain gauges 42 illustrated in FIGS. 2–4 may then be suitably assembled or bonded with the diaphragm 34 at the bottom of the seat.

In this method of forming the pressure tube itself, the resulting plastically deformed diaphragm 34 is automatically smoothly blended with the remainder of the undeformed tube. More specifically, as illustrated in FIGS. 2 and 5, the tube further includes a forward or upstream blend 48 and a corresponding downstream or aft blend 50 disposed on opposite longitudinal sides of the diaphragm 34 along the tube inner surface. The tube blends 48,50 taper circumferentially in width to transition the tube from round at its upstream end to flat at the diaphragm 34 and again to round at its downstream end in a smooth transition which minimizes or prevents disruption in the fluid flow therealong.

As shown in FIGS. 2 and 5, the blends 48,50 are generally flat themselves and transition at corresponding fillets along their edges to the undeformed portion of the tube. The tube converges along the forward blend 48 to the diaphragm 34, and then diverges along the aft blend 50 in the downstream direction from the diaphragm. As shown in FIG. 2, the tube blends 48,50 have relatively shallow angles of inclination relative to the longitudinal axis, with those shallow angles being up to about ten degrees, for example, for promoting smooth flow without undesirable flow separation or stagnation which could damage blood or cause clotting thereof.

Since the initial tube 30 has a constant inner diameter with a constant flow area, the plastic deformation of the tube to form the flat diaphragm 34 locally changes the flow area of the tube due to the change in cross section corresponding therewith. In the exemplary embodiment illustrated in FIG. 2, the cross sectional flow area of the tube decreases slightly along the forward blend 48 to a minimum value at the diaphragm 34 and then increases downstream along the aft blend 50.

In alternate embodiments, the inner profile of the tube may be adjusted for maintaining constant flow area therein or otherwise altering flow area as desired. The different flow areas may be obtained by otherwise plastically deforming the tube, or in yet another embodiment, the tube may be cast with any desired internal configuration thereof including various forms of the forward and aft blends adjoining the flat diaphragm 34.

In the exemplary embodiment illustrated in FIGS. 2 and 3, the tube inner surface 38 is continuous and smooth completely across the diaphragm 34 which forms an integral part of the tube inner surface bounding the fluid flow. The tube and diaphragm are preferably a unitary or one piece component initially formed as indicated above with respect to FIG. 6 by deforming the tube and forming the seat 32 therein from outside the tube.

The seat 32 is thereby formed blind and does not extend completely through the tube wall so that the remaining parent titanium material at the bottom of the seat defines the thin diaphragm 34 integrally with the tube, and as a portion of the inner surface thereof. The strain gauges 42 may then be suitably joined, by bonding, sputtering, or otherwise affixing, to the outside of the diaphragm inside the blind seat 32 for measuring changing strain of the diaphragm as it flexes under internal pressure. The measured strain is directly indicative of the pressure of the fluid acting against the diaphragm.

Figure 7:
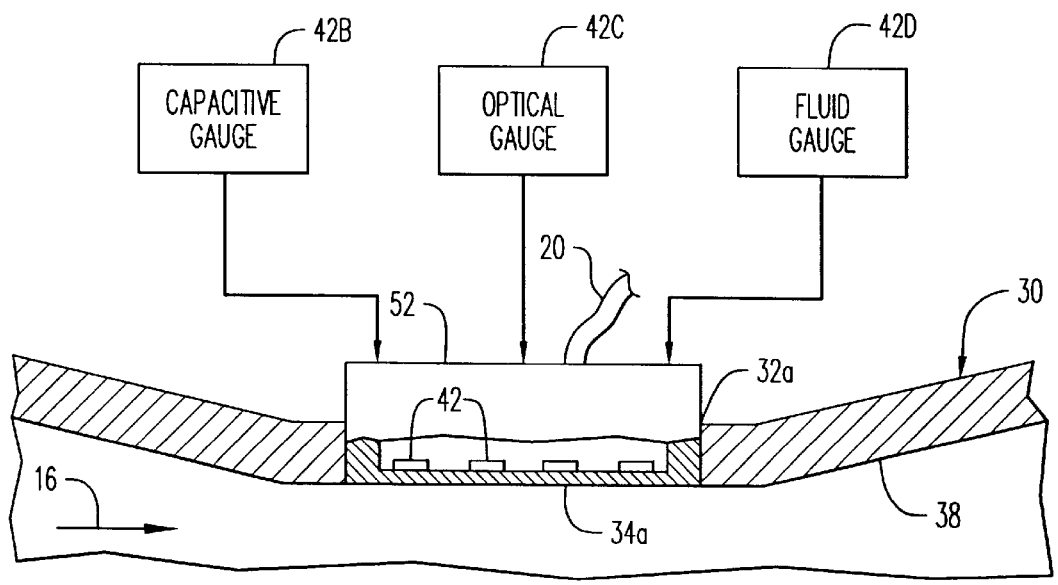
FIG. 7 is a longitudinal sectional view through a tubular pressure sensor in accordance with additional embodiments of the present invention.

FIG. 7 illustrates an alternate embodiment of the pressure sensor illustrated in FIG. 2 wherein the tube 30 and diaphragm, designated 34a, are separate and discrete components and the diaphragm is fixedly disposed through the tube wall. The seat, designated 32a, is a well or cavity suitably formed completely through the tube wall, with the diaphragm 34a being affixed in the well for being continuous and flush with the tube inner surface 38.

In this embodiment, the diaphragm 34a may be an integral portion of a sensor block 52 which may be suitably premanufactured to include the thin, flat diaphragm 34a at its base, with the strain gauges 42 disposed atop the diaphragm and fully encased for protection from the environment. The through-seat 32a may be specifically sized for closely receiving the block 52 which may be suitably bonded therein using an adhesive, for example.

The sensor block 52 may be in the form of a conventional Micro-Electro-Mechanical-System (MEMS) sensor. MEMS sensors are mass produced from single silicon wafers, and have high pressure sensitivity.

In the exemplary embodiment illustrated in FIG. 2, the tube 30 is cylindrical, with the inner surface 38 thereof defining a straight conduit 40 for channeling the fluid in a straight flowpath therethrough. This configuration is particularly advantageous for pumping blood without creating stagnation regions in which clotting may occur.

As shown in FIG. 2, the fluid 16 flows straight past the diaphragm 34 without obstruction or disruption therefrom. The fluid converges along the forward blend 48 for flowing smoothly across the diaphragm and then diverges along the aft blend 50. By maintaining a suitably shallow divergence angle along the aft blend 50, flow separation is prevented and undesirable flow stagnation is avoided for preventing damage to the blood fluid 16.

Figure 8:
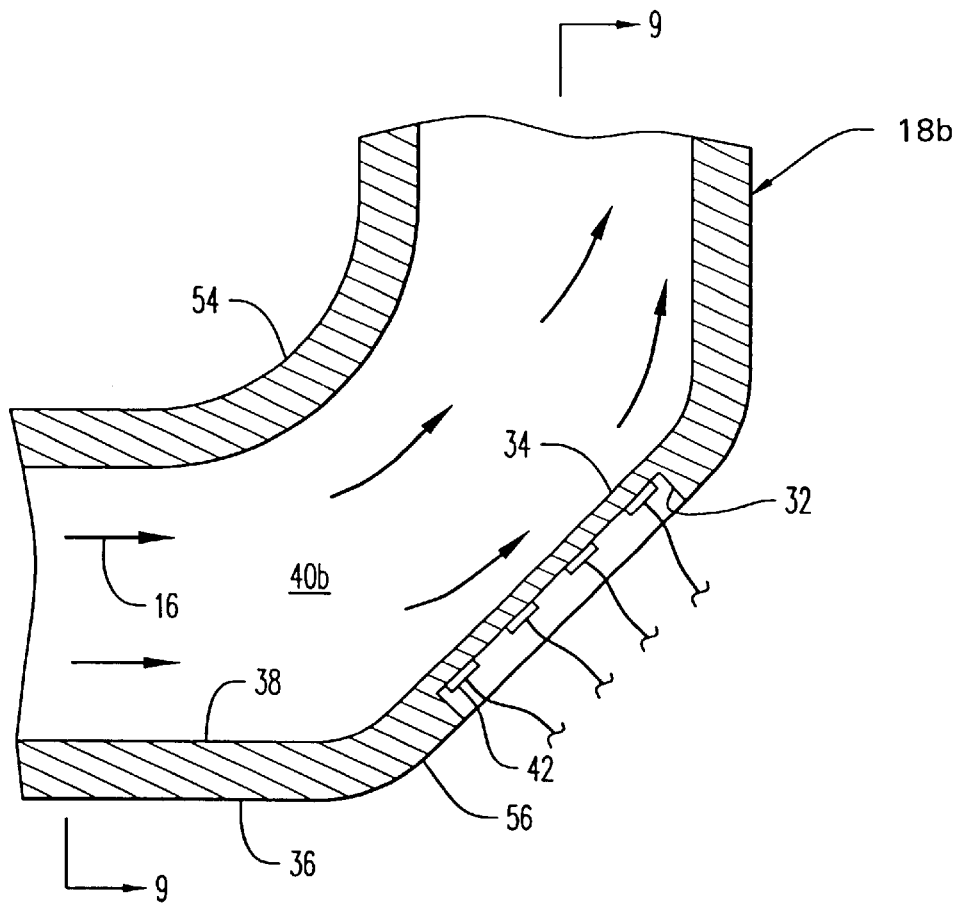
FIG. 8 is a longitudinal sectional view through a pressure sensor in the form of an elbow in accordance with another embodiment of the present invention.
Figure 9:
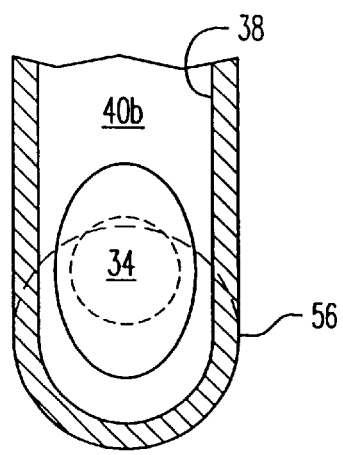
FIG. 9 is an elevational sectional view through the pressure sensor illustrated in FIG. 8 and taken along line 9—9.

FIGS. 8 and 9 illustrate another embodiment of the pressure sensor wherein the tube, designated 18b, defines an elbow which bends the fluid 16 in a ninety degree turn, although the turn may have any suitable angular degree. The tube inner surface 38 defines a corresponding bent conduit, designated 40b, for channeling the fluid therethrough.

The elbow tube 18b includes an inner bend 54 and a radially opposite outer bend 56 which has a larger radius of curvature. The diaphragm 34 is preferably disposed in the outer bend in line-of-sight with the tubular portion of the conduit upstream from the bend. And, the flat diaphragm 34 has an elliptical perimeter which smoothly blends with the arcuate tube inner surface.

In this way, the flow 16 is directed along the diaphragm 34 as it turns along the outer bend for changing direction. Since the outer bend 56 has a larger turning radius than the inner bend 54, the introduction of the flat diaphragm 34 therein can blend more smoothly with the tube inner surface to prevent undesirable flow stagnation or separation which could otherwise lead to blood clotting or damage.

Moreover, at this outer bend 56, the inner surface turns in toward the flowpath so that the fluid's momentum keeps the flow impinging on the diaphragm 34, which ensures that the flow remains attached to the surface rather than becoming separated from the surface.

It is preferable to maintain the arcuate profile of the inner bend 54 unaltered for ensuring smooth flow of the fluid through the elbow without causing undesirable flow separation thereat.

The various embodiments of the pressure sensor 18 disclosed above permit undisrupted flow of the fluid 16 therethrough while measuring pressure thereof at the integral flat diaphragm. The fluid 16 is pumped under pressure through the tube, with the pressure being effected initially by the natural heart 10 illustrated in FIG. 1 for in turn being further pressurized by the heart pump 12 in the exemplary embodiment.

The pressure of the fluid inside the tube creates strain in the diaphragm, as well as in the tube itself, with the strain being directed both longitudinally and circumferentially, or laterally, across the diaphragm. By measuring the strain in the diaphragm using the several strain gauges 42, a corresponding indication of pressure of the fluid at the diaphragm may be obtained.

Strain-based pressure sensors include strain gauges which may be arranged in various configurations atop the diaphragm for detecting tensile and compressive strains therein. An edge supported diaphragm is stiffer at its perimeter than at its center and elastically deforms with greater deflection at its center. The strain gauges near the diaphragm center typically measure tensile strain, with the strain gauges near the diaphragm perimeter measuring compressive strain. The strain gauges are typically configured in a Wheatstone bridge for balanced operation thereof. Such configuration reduces undesirable strain noise due to any bending of the pressure tube itself as opposed to strain in the diaphragm.

Strain noise is also reduced by incorporating the flat diaphragm in the annular tube. Annular tubes are inherently stiff or rigid, and provide a fixed mount for the relatively flexible diaphragm. Thus strain magnitude in the diaphragm is significantly greater than in the tube itself under pressure.

If desired, the pressure tube may be additionally stiffened around the seat and diaphragm in various manners to improve strain isolation of the diaphragm from the tube. For example, FIG. 2 illustrates a rigid collar 58 attached to the tube, and configured in the form of an electrical pin connector to which the cable 20 may be removably attached.

Although pressure may be accurately measured inside the flow tube by measuring strain in the flat diaphragm as it flexes, pressure may be also measured by otherwise measuring flexure or displacement of the diaphragm.

For example, FIG. 7 illustrates schematically a capacitive gauge, designated 42B, which replaces the strain gauges 42 to measure displacement of the flat diaphragm as it flexes under pressure. The diaphragm is configured to form one of two capacitor plates, with the other plate being maintained stationary, so that displacement therebetween changes capacitance, and is indicative of diaphragm flexure and pressure inside the tube. Conventional capacitive displacement sensors may be modified for use with the flat diaphragm.

Another type of flexure measuring gauge is an optical gauge, designated 42C in FIG. 7, which replaces the strain gauges. In the optical gauge, light is transmitted across the flat diaphragm to illuminate its outer surface. The intensity of light reflected therefrom is detected by a photodiode and is representative of the number of fractional wavelengths, and in turn is representative of diaphragm displacement under pressure. A conventional optical sensor which may be adapted for use with the flat diaphragm is an optical Fabry-Perot pressure sensor.

Another type of flexure measuring gauge is a fluid sensor or gauge, designated 42D in FIG. 7, which replaces the strain gauges. In the fluid gauge, a secondary fluid is contained in a closed cavity behind the flat diaphragm. Displacement of the diaphragm displaces the secondary fluid causing a change in pressure in the cavity which can be measured by any type of pressure sensor. The cavity pressure is then indicative of diaphragm flexure, and in turn pressure of the fluid in the tube.

Figure 10:
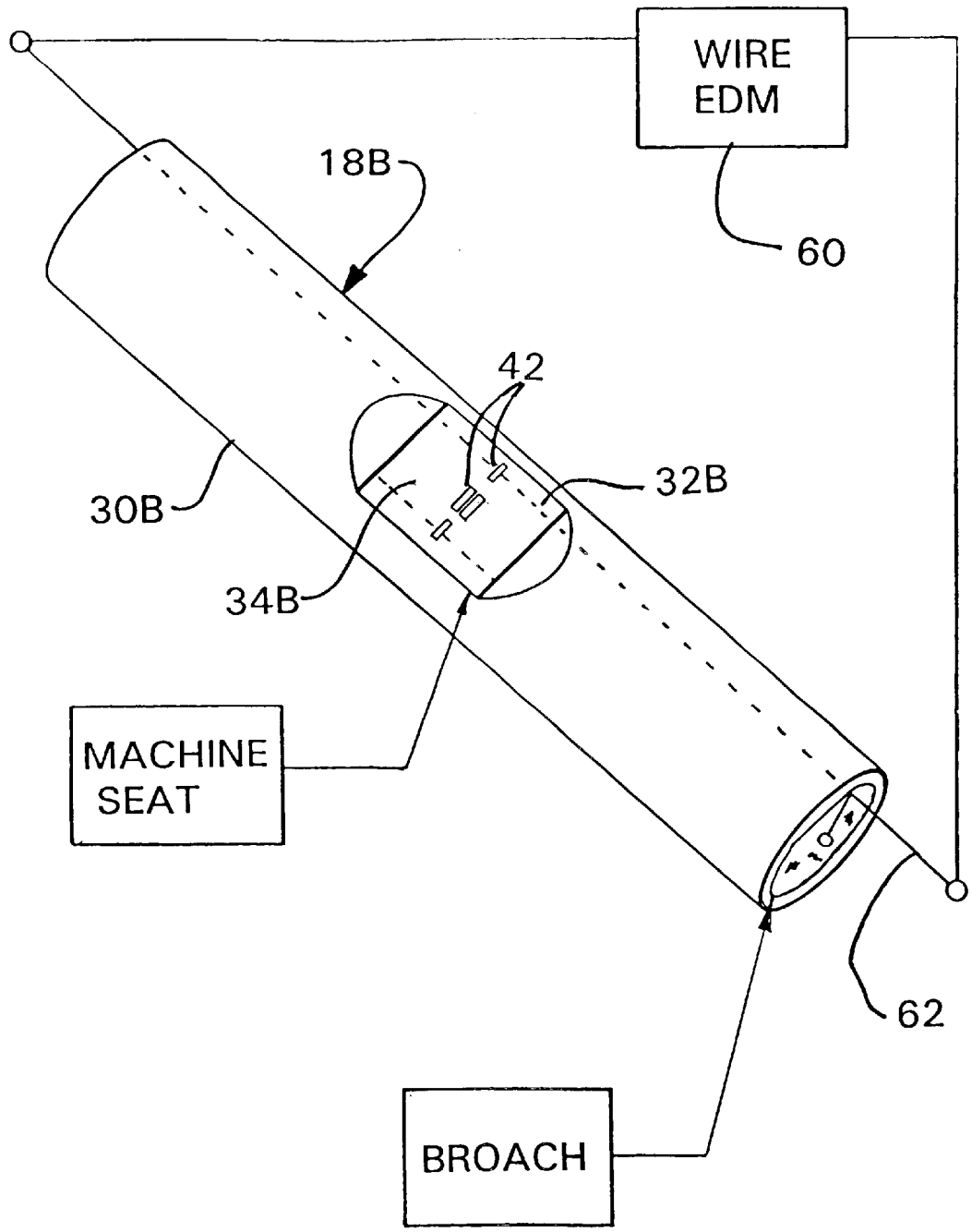
FIG. 10 is a schematic representation of a pressure sensor in accordance with another embodiment of the present invention, and includes exemplary methods of manufacturing.
Figure 11:
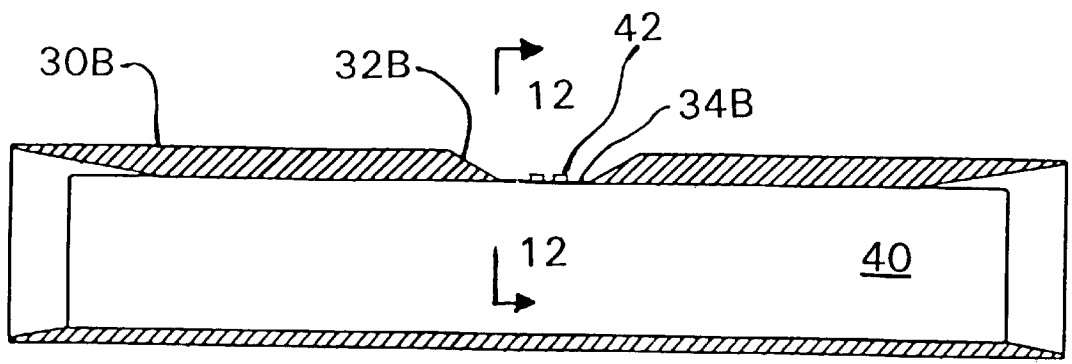
FIG. 11 is an axial sectional view of the pressure sensor illustrated in FIG. 10 upon manufacture thereof.
Figure 12:
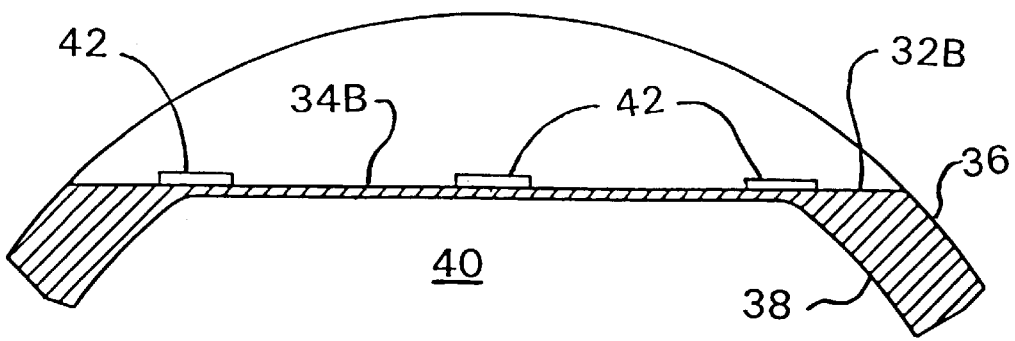
FIG. 12 is a radial sectional view of a portion of the pressure sensor illustrated in FIG. 1 1 and taken generally along line 12—12.

Illustrated in FIGS. 10–12 is yet another embodiment of the pressure sensor, designated 18B. As indicated above, the seat and diaphragm may be rectangular instead of circular for providing enhanced sensitivity and accuracy of pressure measurement. As initially shown in FIG. 10, the seat 32B is disposed in the wall of the tube 30B and preferably extends as a notch completely thereacross for being open at circumferentially opposite ends.

The planar diaphragm 34B is disposed in the seat and forms a chord blending circumferentially with the arcuate inner surface 38 of the tube as illustrated in FIG. 12.

The diaphragm is thinner than the tube wall for being elastically flexible under internal fluid pressure. The strain gauges 42 are disposed atop the diaphragm for measuring strain therein as the thin diaphragm flexes under internal pressure of fluid flowing through the tube during operation.

The pressure sensor 18B having the rectangular diaphragm operates in the same manner as the pressure sensor described above having the circular diaphragm. However, a rectangular diaphragm has a correspondingly different perimeter interface where it joins the tube wall, and thusly experiences different strain and stress as the diaphragm bends under pressure. The rectangular diaphragm effects larger strain than the circular diaphragm for the same chord length and under the same fluid pressure for improving sensitivity and accuracy of pressure measurement.

In the preferred embodiment illustrated in FIG. 12, the diaphragm 34B is again integrally joined to the seat 32B in a unitary combination, and is substantially flat around the perimeter of the seat without being recessed in a well therein. The diaphragm is preferably coplanar with the seat at opposite circumferential ends of the chord so that the diaphragm transitions from a relatively thin plate to the thick wall of the tube which rigidly supports the diaphragm around its perimeter. The diaphragm and seat collectively provide an exposed flat surface or notch across a chord of the tube upon which the flexure measuring gauge may be mounted.

As shown in FIGS. 10 and 12, a pair of outboard strain gauges 42 are disposed at corresponding opposite ends of the chord, and an inboard pair of strain gauges 42 are disposed centrally therebetween along the chord between the outboard pair of strain gauges.

A particular advantage of using the coplanar, flat diaphragm and integral seat is that the outboard strain gauges may now bridge the diaphragm 34B and the tube wall at the chord opposite ends. Since the tube wall supports the relatively thin rectangular diaphragm, the diaphragm flexes or bends under pressure from the fluid inside the tube and generates strain at the joint or interface between the circumferentially opposite ends of the diaphragm and the supporting tube wall. By mounting the outboard strain gauges atop the chord-wall interface, a maximum level of strain may be measured thereat for increasing sensitivity of pressure measurement.

The pair of inboard strain gauges are preferably disposed generally in-line with the outboard strain gauges, with the inboard strain gauges being mounted axially side by side. In this configuration, all four strain gauges measure strain predominantly along the direction of the chord, or along the circumferential or hoop direction around the tube at the diaphragm.

The outboard gauges measure strain at the perimeter of the supported diaphragm, with the inboard gauges measuring strain at the center of the diaphragm which deflects outwardly under fluid pressure. In this way, the strain gauges are placed at locations of maximum strain for increasing the sensitivity to strain, and therefore, pressure measurement. In alternate embodiments, the strain gauges may be otherwise disposed on the flat rectangular diaphragm as desired.

As shown in FIGS. 11 and 12, the tube 30B has a generally D-shaped bore 40 extending axially from opposite axial ends of the rectangular diaphragm 34B and between the opposite axial ends of the tube. The resulting D-shaped transverse profile of the tube inner surface has a straight chord section matching the straight chord of the flat diaphragm, and a circular arcuate section corresponding with the remainder of the otherwise tubular bore. In this way, the flat diaphragm transitions or blends smoothly with the tubular bore which is particularly desirable for pumping blood through the pressure sensor and minimizing any blood damage during operation.

As shown in FIG. 11, the tube bore 40 remains D-shaped in profile for substantially the full axial length of the tube and then transitions to circular profiles at the axially opposite ends of the tube to provide smooth blending with tubular connections when introduced into a pumping system such as the exemplary blood pump disclosed above.

FIG. 10 illustrates schematically two exemplary methods of forming the pressure sensor 18B corresponding with the rectangular diaphragm thereof. The tube is initially provided with a generally D-shaped bore as indicated above, and may otherwise have a relatively constant thickness tube wall. Conventional machining may then be used for removing material from the outer surface of the tube to form a notch defined by the seat 32B and diaphragm 34B in a common machining operation which leaves a flat surface across one side of the tube near its center. For example, the notch may be formed by milling, electrical discharge machining, or any other suitable manufacturing process. The several strain gauges 42 may then be suitable mounted atop the diaphragm in the same manner as described above for the circular diaphragm embodiment.

The exemplary rectangular seat 32B illustrated in FIG. 10 preferably includes tapered portions extending axially away from the rectangular diaphragm for providing additional clearance for unobstructed sputtering of the strain gauges atop the diaphragm, if desired.

Consistency of operation of multiple pressure sensors produced for production requires corresponding consistency of manufacture of the pressure sensors. Dimensional consistency may be obtained by forming the tube bore 40, illustrated in FIGS. 11 and 12, by conventional wire electrical discharge machining (EDM). A conventional EDM apparatus 60 is illustrated schematically in FIG. 10 and includes a corresponding EDM wire 62 which may be used for precisely forming the tube bore.

The tube itself may be in the initial form of a solid bar having an axial through-hole drilled therein, or a correspondingly thick walled tube. The EDM wire 62 is threaded through the initial small bore of the tube and then used for accurately machining the desired D-profile of the tube bore for obtaining a preferably constant thickness tube wall and a flat inner surface of the diaphragm. The outer surface of the tube is suitably machined using any conventional machine tool for removing metal therefrom so that the resulting rectangular diaphragm 34B is relatively thin with a preferably constant thickness over the full extent thereof within its rectangular perimeter. The typical recast layer remaining inside the tube bore following the EDM operation may then be suitably removed for providing a smooth surface finish inside the tube.

In an alternate method of forming the D-profiled tube bore, a relatively thick walled tube may be conventionally broached using series of cutting tools increasing in size for removing material from the inside of the tube to the final D-shaped profile thereof. The broaching process not only ensures accurate dimensions of the tube wall thickness and thickness of the rectangular diaphragm, but results in a smooth surface finish requiring little if any final polishing for achieving the desired surface finish for use in a blood pressure sensor for the preferred application of the invention.

In yet another embodiment, the preferred D-shaped tube bore may be originally provided in an extruded tube. Extrusion is a conventional process effective for producing simple to complex cross sections with precise tolerances and dimensional accuracy, and may be used where economically feasible. Extrusion may then be used to form the original tube with the desired D-shaped internal bore, with the seat and diaphragm then being machined in the outer surface of the tube. And, the end-transitions of the D-profile to circular profiles at the tube opposite ends may then be effected in any suitable manner such as by using a conical cutting tool for machining the inner surface of the tube and locally removing the flat chord portions thereof to provide circular inlet and outlet ends of the tube.

Notching the diaphragm and seat across the tube provides many advantages over the blind well embodiment. The diaphragm can be machined thin over its full surface area with high precision. The diaphragm can then be flat, even, and smooth, with constant thickness. Both outer and inner surfaces of the diaphragm are flat and may be easily polished for additional smoothness as desired for better cooperating with the flexure gauges for example.

Notching the diaphragm across the tube wall also reduces or eliminates any distortion in the resulting thin section thereof. This also reduces problems due to welded diaphragms or otherwise assembled diaphragms which do not enjoy the benefits of integral or unitary construction of the notched diaphragm.

Both the circular and rectangular diaphragm embodiments of the pressure sensor described above enjoy similar advantages for measuring internal fluid pressure of the corresponding tubes. The various methods of forming the different embodiments of the pressure sensors have different advantages in dimensional accuracy, and simplicity of manufacture, and corresponding cost therefor.

The open or notched seat embodiment described above has certain advantages over the blind hole embodiment, including:

1. it is easier to machine and polish the planar surface of the open seat than the surface at the bottom of the closed blind hole;
2. it is easier to mount the strain gauges on the flat surface of the open seat than in the corner at the base of the blind hole;
3. the strain gauges can straddle the edge of the diaphragm in the open seat to measure strain at the point of maximum strain at the diaphragm perimeter, whereas the gauges in the blind hole must be offset inside the corner thereof surrounding the diaphragm; and
4. the open seat has a continuous planar surface, shared by the top surface of the diaphragm and the coplanar portions of the supporting tube wall.

The rectangular or square diaphragm embodiment described above has certain advantages over the round diaphragm embodiment, including:

1. more diaphragm area may be obtained for a square diaphragm over a round diaphragm for a given chord length across the tube;
2. this larger diaphragm produces a larger deflection and overall larger strain signal;
3. a rectangular diaphragm produces a larger strain signal than a square diaphragm for a given width, and can be longer along the axial axis of the tube for increasing strain signal, without increasing chord length or reducing tube flow area corresponding thereto; and
4. the strain gauges can be mounted at the points of maximum strain at the midpoints of the perimeter edges of the diaphragm where strain is concentrated to provide a larger yet strain signal.

The flat diaphragm pressure sensor therefore enjoys a substantial increase in sensitivity and resolution, and correspondingly high signal-to-noise ratio, as opposed to arcuate diaphragm based pressure sensors.

This configuration allows the flat diaphragm to be integrated into a cannula tube with a resulting pressure signal being insensitive to noise due to mechanical strain in the tube. Since the strain gauges themselves are separated from the fluid inside the tube by the intervening diaphragm, the strain gauges are protected from the fluid flowing through the tube, and vice versa.

For the exemplary embodiment of channeling blood to the heart pump illustrated in FIG. 1, the entire inner surface of the tube remains smooth without undesirable discontinuities or cavities therein which could cause blood stagnation, separation, recirculation, clotting, or damage thereto. Furthermore, the smooth wall will not adversely reduce shear stress in the blood fluid which would otherwise contribute to the initiation of undesirable blood clotting, coagulation, or thrombus formation.

The pressure sensor is relatively simple, compact, stable over time, and highly accurate for use in implantation in a human body for the long term control of the heart pump 12.

Although the pressure sensor has been disclosed above in various embodiments, including specifically for use in measuring blood pressure, it may be used in other applications for measuring pressure in other fluids such as liquids or gasses. It may be readily incorporated in any fluid channeling device such as pipes or catheters having otherwise cylindrical or circular internal wall surfaces.

While there have been described herein what are considered to be preferred and exemplary embodiments of the present invention, other modifications of the invention shall be apparent to those skilled in the art from the teachings herein, and it is, therefore, desired to be secured in the appended claims all such modifications as fall within the true spirit and scope of the invention.

Accordingly, what is desired to be secured by Letters Patent of the United States is the invention as defined and differentiated in the following claims in which we claim:

1. A pressure sensor comprising:

a tube for channeling fluid therethrough;

a notched seat disposed in a wall of said tube, and being open at circumferentially opposite ends;

a planar diaphragm disposed in said seat and being thinner than said tube wall, and forming a chord blending circumferentially with an arcuate inner surface of said tube; and a gauge mounted in said seat above said diaphragm for measuring flexure thereof under pressure of said fluid inside said tube.

2. A sensor according to claim 1 wherein said diaphragm is integrally joined to said seat and is substantially flat around the perimeter thereof.

3. A sensor according to claim 2 wherein said diaphragm is rectangular.

4. A sensor according to claim 3 wherein said diaphragm is coplanar with said seat at opposite ends of said chord.

5. A sensor according to claim 4 wherein said flexure measuring gauge comprises a plurality of strain gauges mounted atop said diaphragm for measuring strain therein due to flexing thereof.

6. A sensor according to claim 5 wherein an outboard pair of said strain gauges are disposed at corresponding opposite ends of said chord.

7. A sensor according to claim 6 wherein said outboard strain gauges bridge said diaphragm and tube wall at said chord opposite ends.

8. A sensor according to claim 6 wherein an inboard pair of said strain gauges are disposed along said chord between said outboard pair of strain gauges.

9. A sensor according to claim 4 wherein said tube has a generally D-shaped bore extending axially from opposite ends of said diaphragm.

10. A sensor according to claim 9 wherein said tube bore transitions to circular profiles at axially opposite ends of said tube.

11. A method of forming said pressure sensor according to claim 1 comprising:

providing said tube with a generally D-shaped bore;

removing material from an outer surface of said tube to form said notched seat and diaphragm; and mounting said flexure measuring gauge atop said diaphragm.

12. A method according to claim 11 wherein said tube bore is formed by wire electrical discharge machining.

13. A method according to claim 11 wherein said tube bore is formed by broaching.

\* \* \* \* \*